US011628263B2

(12) United States Patent
Klurfeld et al.

(10) Patent No.: US 11,628,263 B2
(45) Date of Patent: Apr. 18, 2023

(54) TRI-STATE COMPACT MODULAR INHALER, VAPORIZER

(71) Applicants: Peter Daniel Klurfeld, Encino, CA (US); Douglas Cohen, Venice, CA (US); Elliott Galynsky, Van Nuys, CA (US)

(72) Inventors: Peter Daniel Klurfeld, Encino, CA (US); Douglas Cohen, Venice, CA (US); Elliott Galynsky, Van Nuys, CA (US)

( * ) Notice: Subject to any disclaimer, the term of this patent is extended or adjusted under 35 U.S.C. 154(b) by 495 days.

(21) Appl. No.: 16/806,198

(22) Filed: Mar. 2, 2020

(65) Prior Publication Data

US 2021/0268210 A1 Sep. 2, 2021

(51) Int. Cl.

*A61M 11/00* (2006.01)
*A61M 15/00* (2006.01)
*A61M 15/06* (2006.01)

(52) U.S. Cl.

CPC ...... *A61M 11/007* (2014.02); *A61M 15/0068* (2014.02); *A61M 15/06* (2013.01); *A61M 2202/0007* (2013.01); *A61M 2205/127* (2013.01)

(58) Field of Classification Search

CPC ............ A61M 11/007; A61M 15/0068; A61M 15/06; A61M 2202/0007; A61M 2205/127; A61M 2205/123; A61M 2205/8206; A61M 2205/583; A24F 40/20; A24F 40/40; A24F 40/42

See application file for complete search history.

(56) References Cited

U.S. PATENT DOCUMENTS 1,870,558 A * 8/1932 Darby .................. A61M 15/08 128/203.21
2015/0136158 A1* 5/2015 Stevens ................ A61M 15/06 131/329
2015/0245659 A1* 9/2015 DePiano ............... B21D 53/06 392/397
2016/0287816 A1* 10/2016 Eksouzian .......... A61M 11/042
(Continued)

FOREIGN PATENT DOCUMENTS

WO WO-9204928 A2 * 4/1992

*Primary Examiner* — Nilay J Shah
(74) *Attorney, Agent, or Firm* — William J. Benman; Benman, Brown & Williams

(57) ABSTRACT

A compact modular multifunctional inhalation device including a housing having an inlet port and an outlet port; a removable cartridge module adapted to seat within the housing, the cartridge including: a tray within the cartridge for holding a solid inhalant, a heating element mounted within the cartridge above and through the tray for heating the inhalant; and a removable modular electronic circuit adapted to seat within the housing to provide electrical current to the heating element. The heating element is a coil mounted within a chamber in thermal proximity to the solid inhalant. A quartz rod is mounted within the coil. A plunger is mounted within the cartridge to translate therein and compact the solid inhalant. In an alternative embodiment, dual channels and outlet ports are mounted in communication with an inlet port. In another embodiment, the cartridge is a split chamber cartridge with a split plunger mounted therein.

9 Claims, 12 Drawing Sheets

(56) References Cited

U.S. PATENT DOCUMENTS

| | | | | |
|---|---|---|---|---|
| 2017/0231283 | A1* | 8/2017 | Gadas | A24F 7/02 |
| | | | | 131/329 |
| 2018/0168231 | A1* | 6/2018 | Reevell | A61M 11/042 |
| 2019/0053540 | A1* | 2/2019 | Baker | A24F 40/60 |
| 2019/0373679 | A1* | 12/2019 | Fu | H01R 13/521 |

* cited by examiner

TRI-STATE COMPACT MODULAR INHALER, VAPORIZER

BACKGROUND OF THE INVENTION

Field of the Invention

The present invention relates to health-related devices. More specifically, this invention relates to inhalers and vaporizers.

Description of the Related Art

An inhaler is a device used for delivering medication via inhalation. Inhalers typically use a compressed-gas propellant to deliver a metered dose of medicine. When the inhaler is activated, a fixed amount of the medicine is suspended in the propellant and is expelled from the mouthpiece of the inhaler. Vaporizers are devices used to turn active ingredients of plant material and/or other herbs or blends, chemical mixtures i.e. salt solutions or other synthetic compounds to vapor for the purpose of inhalation. An atomizer is a device, typically electrically connected to a heating element, for emitting water, perfume, or other liquids as a fine spray or vapor.

A need existed in the art for a compact inhaler, vaporizer or atomizer A compact implementation of an inhaler, vaporizer or atomizer would allow for the device to be worn on the body thereby making it available to a patient or user for medical emergencies or simple convenience.

The need in the art was addressed by U.S. patent application Ser. No. 15/264,508 entitled Wearable Multifunctional Inhaler, Vaporizer Watch filed Sep. 13, 2016 by P. D Klurfeld, the teachings of which are incorporated herein by reference. This application disclosed and claimed a novel wearable multifunctional inhaler and vaporizer incorporated into a watch.

However, a need remained in the art for a more compact, versatile and cost effective multifunctional inhaler vaporizer design and construction. That need was addressed by U.S. patent application Ser. No. 16/232,869 filed Dec. 26, 2018 by P. D. Klurfeld et al., the teachings of which are incorporated herein by reference.

While these applications addressed the need in the art for a compact, versatile and cost effective multifunctional inhaler vaporizer, these designs were optimized for liquid inhalant. Those in the art will appreciate that solid inhalant materials offer a stronger more concentrated draw that may be seen as advantageous for certain applications. According, a need remains in the art for an inhaler/vaporizer capable of vaporizing solid inhalants.

SUMMARY OF THE INVENTION

The need in the art is addressed by the compact modular multifunctional inhalation device of the present invention. The inventive device includes a housing having an inlet port and an outlet port; a removable cartridge module adapted to seat within the housing, the cartridge including: a tray within the cartridge for holding a solid inhalant, a heating element mounted within the cartridge above and through the tray for heating the inhalant; and a removable modular electronic circuit adapted to seat within the housing to provide electrical current to the heating element.

In an illustrative embodiment, housing includes an air inlet port and an inhalant outlet port. The heating element is a coil of metal or ceramic having 2-13 loops and a diameter ranging from 1.3 mm to 3.5 mm. The coil is mounted within a chamber in thermal proximity to the solid inhalant. A quartz rod is mounted within the coil. A plunger is mounted within the cartridge to translate therein and compact the solid inhalant.

In an alternative embodiment, an air inlet port is mounted on the cartridge, a vapor outlet port is mounted within the plunger and a channel is provided therebetween within the plunger. The embodiment includes dual channels and outlet ports mounted therein in communication with the inlet port.

In another embodiment, the cartridge is a split chamber cartridge with a split plunger mounted therein.

Yet another embodiment features a measurement glass cover gauge mounted on the cartridge. A draw strength gauge switch is disclosed along with an arrangement for changing the temperature of the coil in response thereto.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
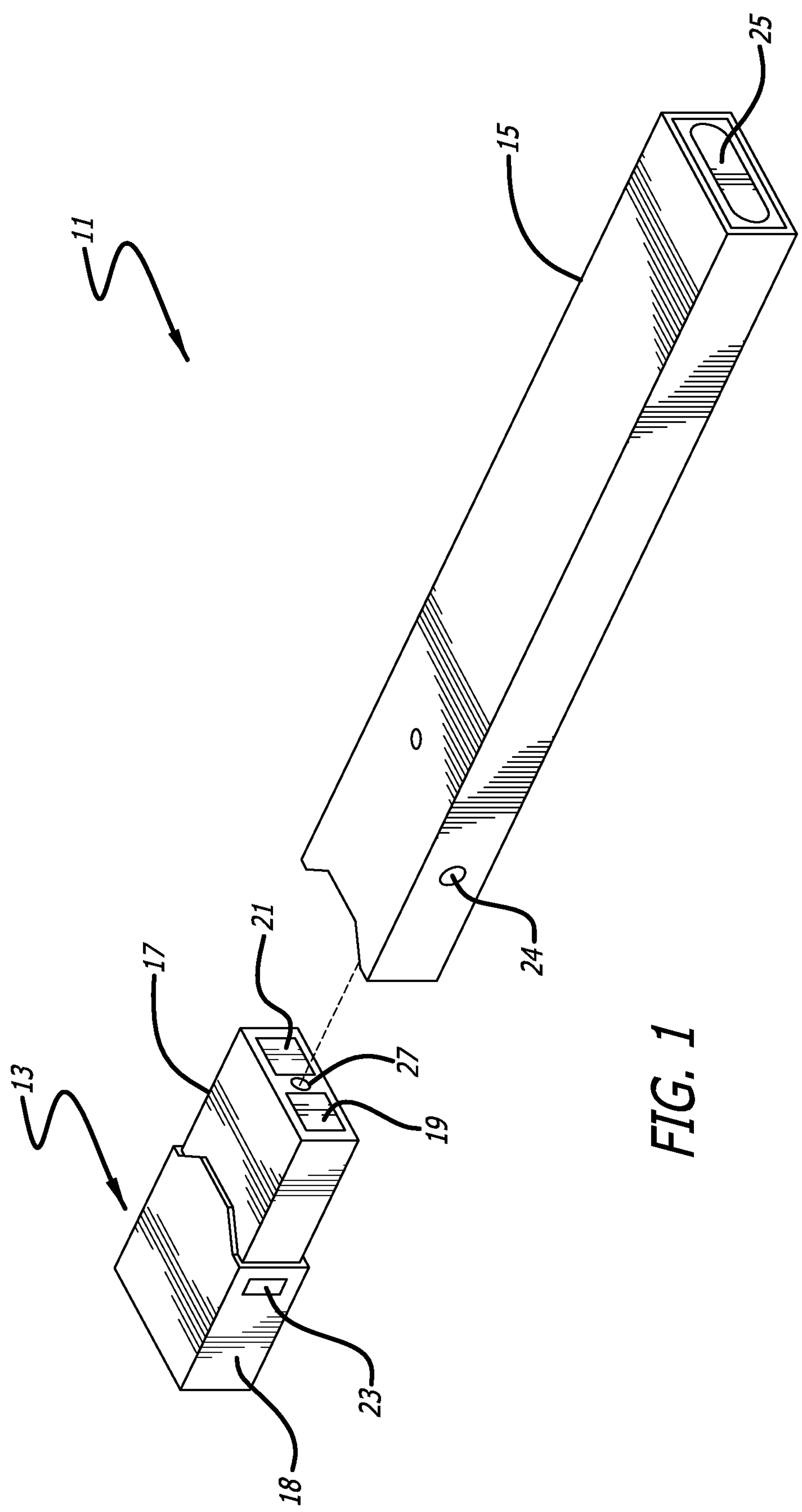
FIG. 1 is a perspective view of a partially disassembled compact modular multifunctional inhalation device of the present invention.

FIG. 1 is a perspective view of a partially disassembled compact modular multifunctional inhalation device of the present invention. The inventive device 11 includes a two piece housing with a vape cartridge 13 and a battery cartridge 15. The vape cartridge 13 is adapted to slide into and electrically connect with the battery cartridge 15. In the embodiment of FIG. 1, the vape cartridge 13 is an elongate rectangular cylinder made of plastic or alloy stainless steel, carbon steel, iron, copper aluminum, or other suitable material and has approximate dimensions of 27×13×5 millimeters to 30×17×8 millimeters and the battery cartridge 15 is an elongate rectangular cylinder adapted to receive the vape cartridge 13 and made of plastic or alloy such as stainless steel, carbon steel, iron, copper, aluminum or other suitable material with approximate dimensions of 75×13×5 mm to 90×18×8 millimeters.

The vape cartridge has an inner housing 17 and an outer shell 18. In the best mode, the inner housing 17 is made of plastic or ceramic or other suitable material and has approximate dimensions of 22×12×4 to 25×15×6.75 millimeters.

Electrical contacts 19 and 21 on the inner housing 17 engage mating contacts (not shown) in the battery cartridge 15. An air inlet 27 is provided in the vape cartridge 13 between the electrical contacts 19 and 21. An air passage 24 is provided on both sides of the vape cartridge 13. Inner housing 17 snaps onto mouthpiece 18 at notch 23.

Figure 2A:
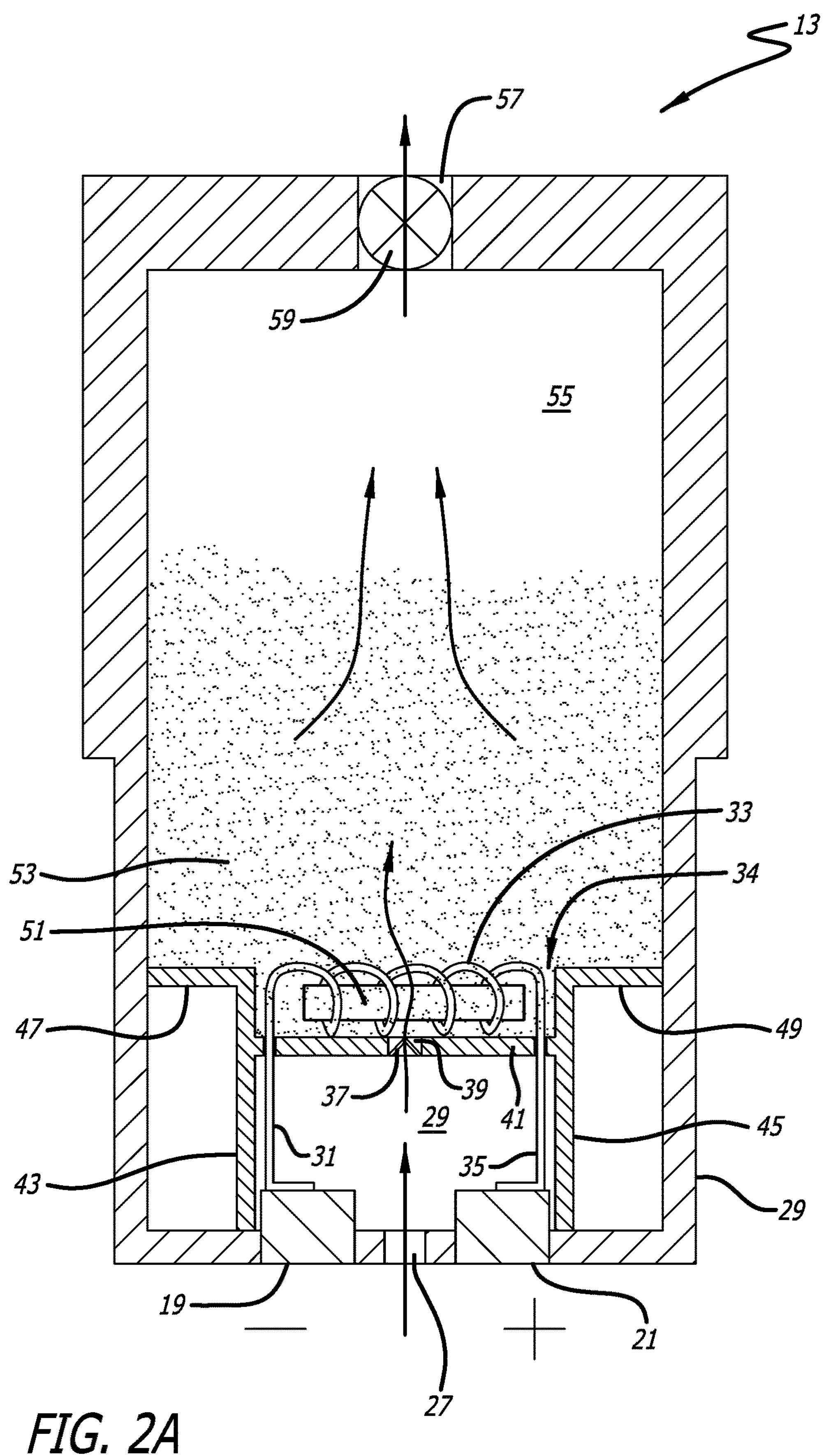
FIG. 2A is a sectional side view of the vape cartridge of the compact modular multi-functional inhalation device of FIG. 1 implemented as a closed cartridge.

FIG. 2A is a sectional side view of the vape cartridge of the compact modular multifunctional inhalation device of FIG. 1. As shown in FIG. 2A, the vape cartridge 13 has an inlet port 27 through which air enters a first chamber 29. The first chamber 29 is defined by a first wall 41 and side walls 43 and 45. The first wall 41 provides a ceiling for first chamber 29 and a floor for a recess 34 in the second chamber 55. The recess is provided in the floor of the second chamber and bounded by first and second floor supports 47 and 49. In the best mode, internal structures 41, 43, 45, 47 and 49 are fabricated of ceramic although other materials may be utilized as will be appreciated by those of ordinary skill in the art.

Air from the chamber 29 enters inhalation chamber 55 regulated by a first one-way valve 37 in an air passage 39. A coil 33 is mounted in the recess 34 in the inhalation chamber 55. The coil 33 has a first lead 31 connected to the first contact 19 and a second lead 35 connected to the second contact 21. The coil 33 is wrapped around a rod 51. In accordance with the present teachings, the coil is made of Kanthal or Nichrome (stainless steel, nickel, and titanium) has a diameter of 1.3 mm-3.5 mm and has 2-13 coils. Its 2 to 13 loops In the best mode, the rod 51 is made of quartz or other suitable material.

A dab or wax of solid inhalant or tobacco 53 is mounted within the second chamber 55. A seal lid or cap 50 is included to seal the top of the chamber 55 and enable it to be opened, refilled and closed. In the illustrative embodiment, the cap is modular, made of rubber or other suitable material and has approximate dimensions of 11×3×2.5 mm to 15×5×5 mm Other materials could be used in the chamber including solid and highly viscous thick oils such as butter, crumble, sauce, rosin, crystals and wax by way of example and without departing from the scope of the present teachings.

A second one-way valve 59 is mounted in an inhalant outlet port 57 mounted at the top of the second chamber 55 in the cap 50.

In operation, an electrical potential is applied to the coil 33 by the battery cartridge 15 via the contacts 19 and 21. This potential causes current to flow through the coil 33 which, in turn, causes the coil to heat and melt the dab of wax 53 filling the second chamber with gas. The gas is then inhaled by the user via the outlet port 59.

Figure 2B:
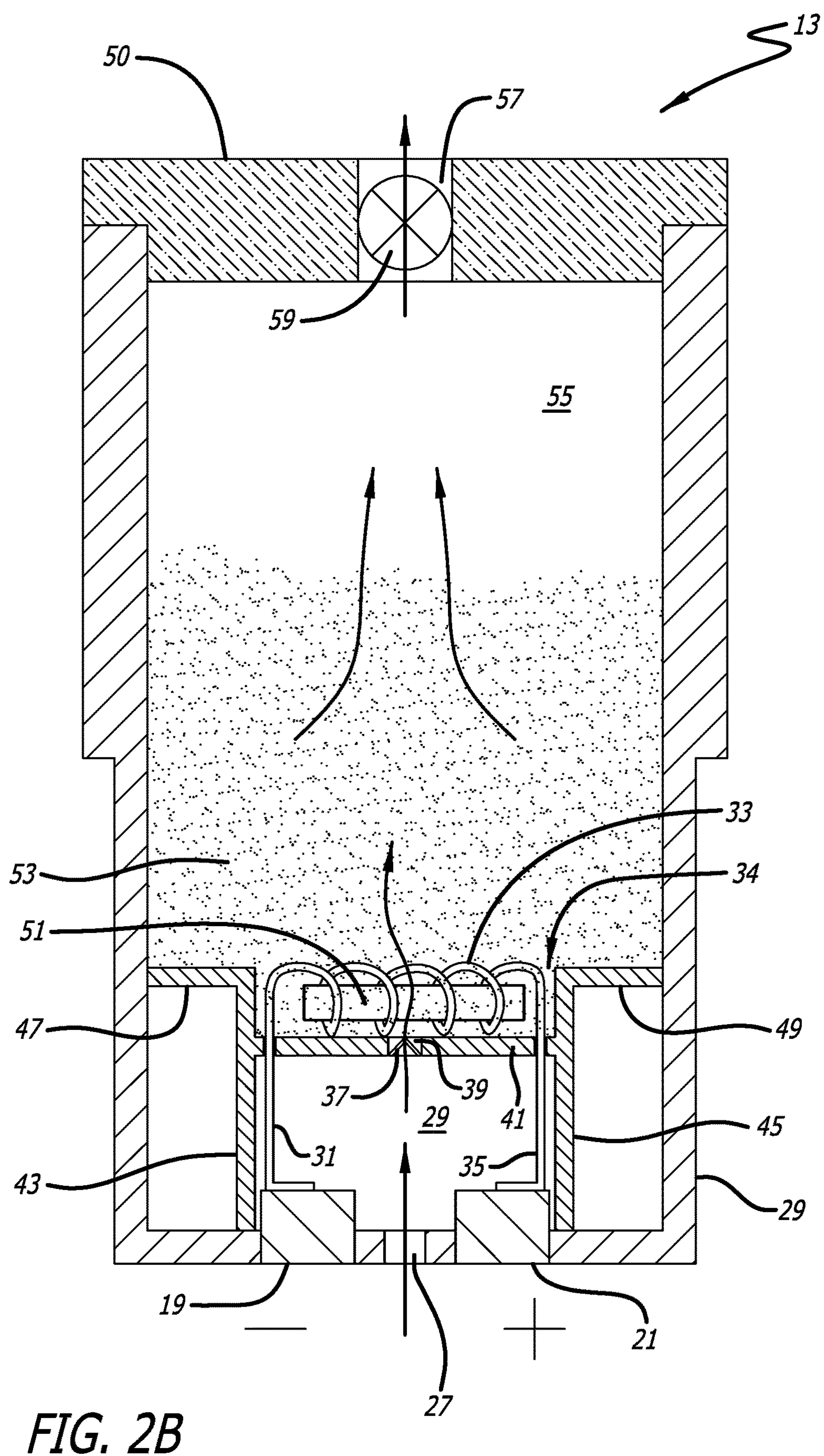
FIG. 2B is a sectional side view of an alternative embodiment of the vape cartridge of the compact modular multifunctional inhalation device of FIG. 1 implemented as an open cartridge with a removable plug.

FIG. 2B is a sectional side view of an alternative embodiment of the vape cartridge of the compact modular multifunctional inhalation device of FIG. 1 implemented as an open cartridge with a removable plug.

Figure 3:
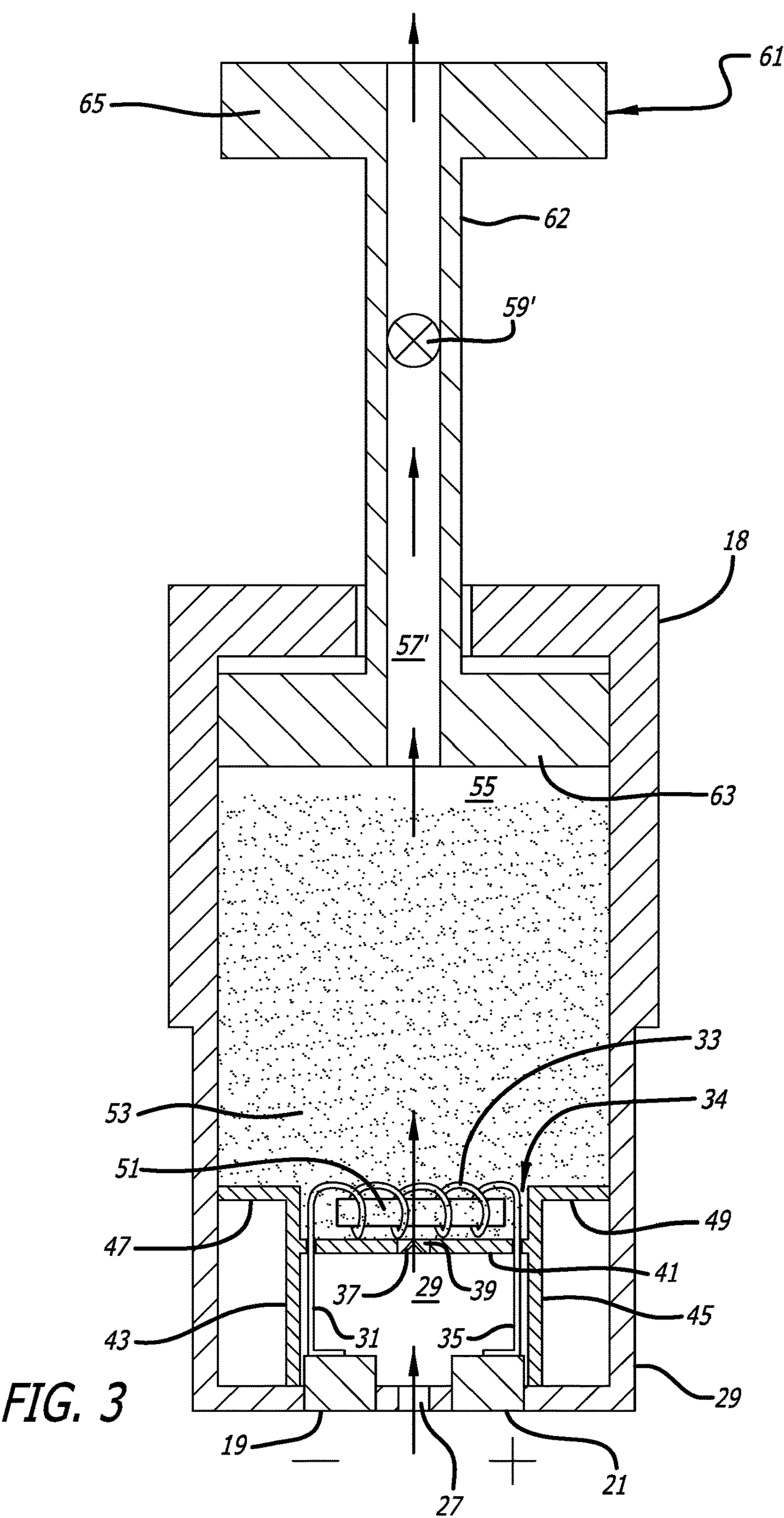
FIG. 3 is a sectional side view of an alternative embodiment of the vape cartridge of the compact modular multifunctional inhalation device depicted in FIGS. 2A and 2B with a plunger in a first position in accordance with the present teachings.

FIG. 3 is a sectional side view of an alternative embodiment of the vape cartridge of the compact modular multifunctional inhalation device depicted in FIG. 2 with a plunger in a first (up) position in accordance with the present teachings.

Figure 4:
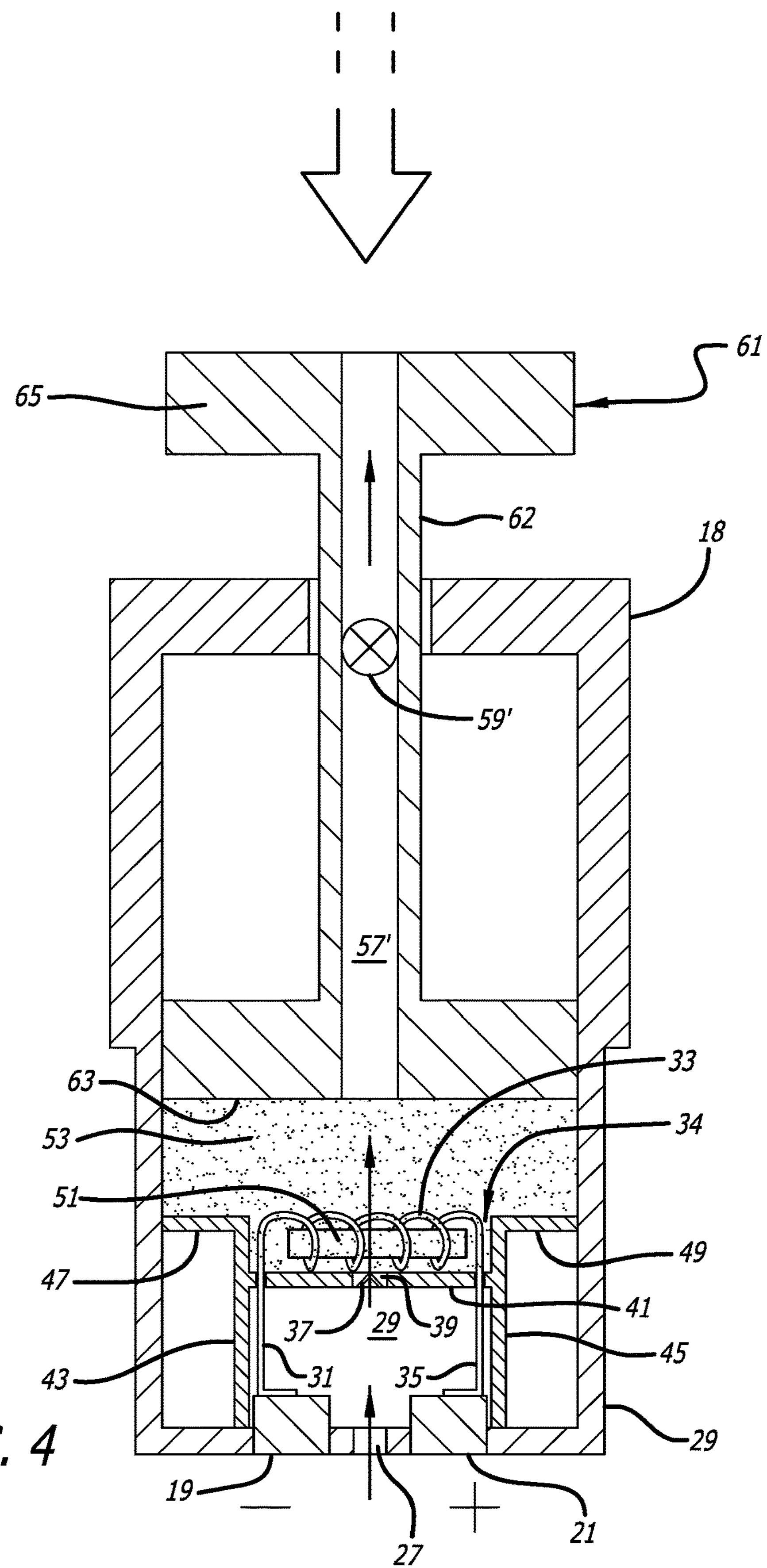
FIG. 4 is a sectional side view of the alternative embodiment of the vape cartridge of the compact modular multifunctional inhalation device depicted in FIG. 3 with the plunger in a second position in accordance with the present teachings.

FIG. 4 is a sectional side view of the alternative embodiment of the vape cartridge of the compact modular multifunctional inhalation device depicted in FIG. 3 with the plunger in a second (down) position in accordance with the present teachings. The plunger 61 is mounted within the cartridge to translate therein and compact the solid inhalant 53. The air outlet port 57' and one way valve 59' are mounted within the stem 62 of the plunger 61 between the bottom and top elements thereof 63 and 65 respectively. In the best mode, the plunger 61 is cylindrical made of ceramic and steel heat treated silicone coated rubber, wood or plastic. (The plunger 61 is shown as an imperfect rectangular prism in FIGS. 1-6 while the plunger 61 is shown as cylindrical in FIGS. 8-10*b*.)

To mitigate clogging of the port 57', a dual channel design discussed below may be employed.

Figure 5:
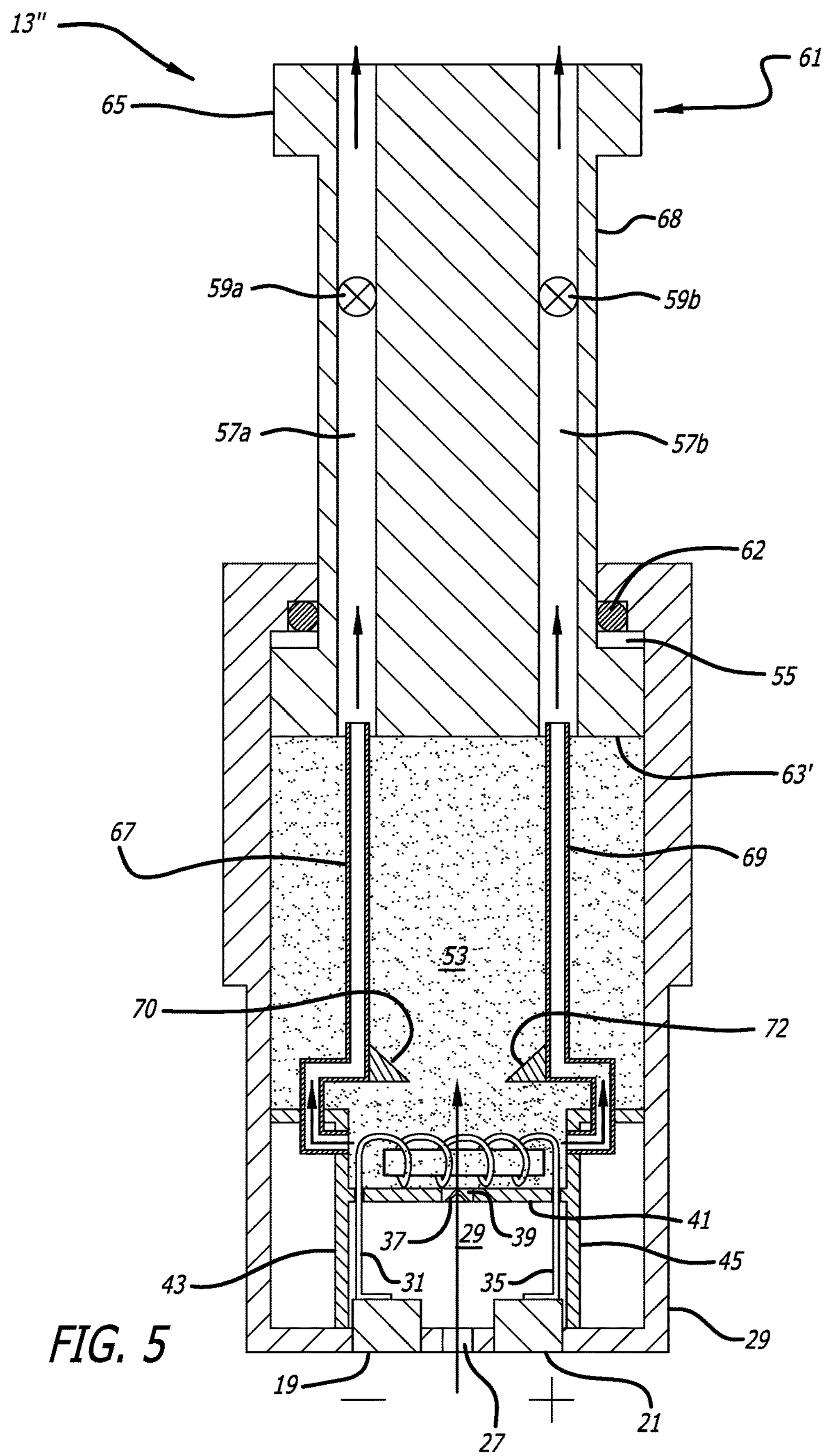
FIG. 5 is a sectional side view of a second alternative embodiment of the vape cartridge of the compact modular multifunctional inhalation device depicted in FIG. 3 with dual inhalation channels through a plunger in a first position in accordance with the present teachings.

FIG. 5 is sectional side view of a second alternative embodiment of the vape cartridge of the compact modular multifunctional inhalation device depicted in FIG. 3 with first and second inhalation channels being provided by first and second conduits 67 and 69, respectively, through a plunger 61' shown in a first position (up) in accordance with the present teachings. The first and second conduits may be fabricated of aluminum, stainless steel, nickel, copper, and iron without departing from the scope of the present teachings.

Figure 6:
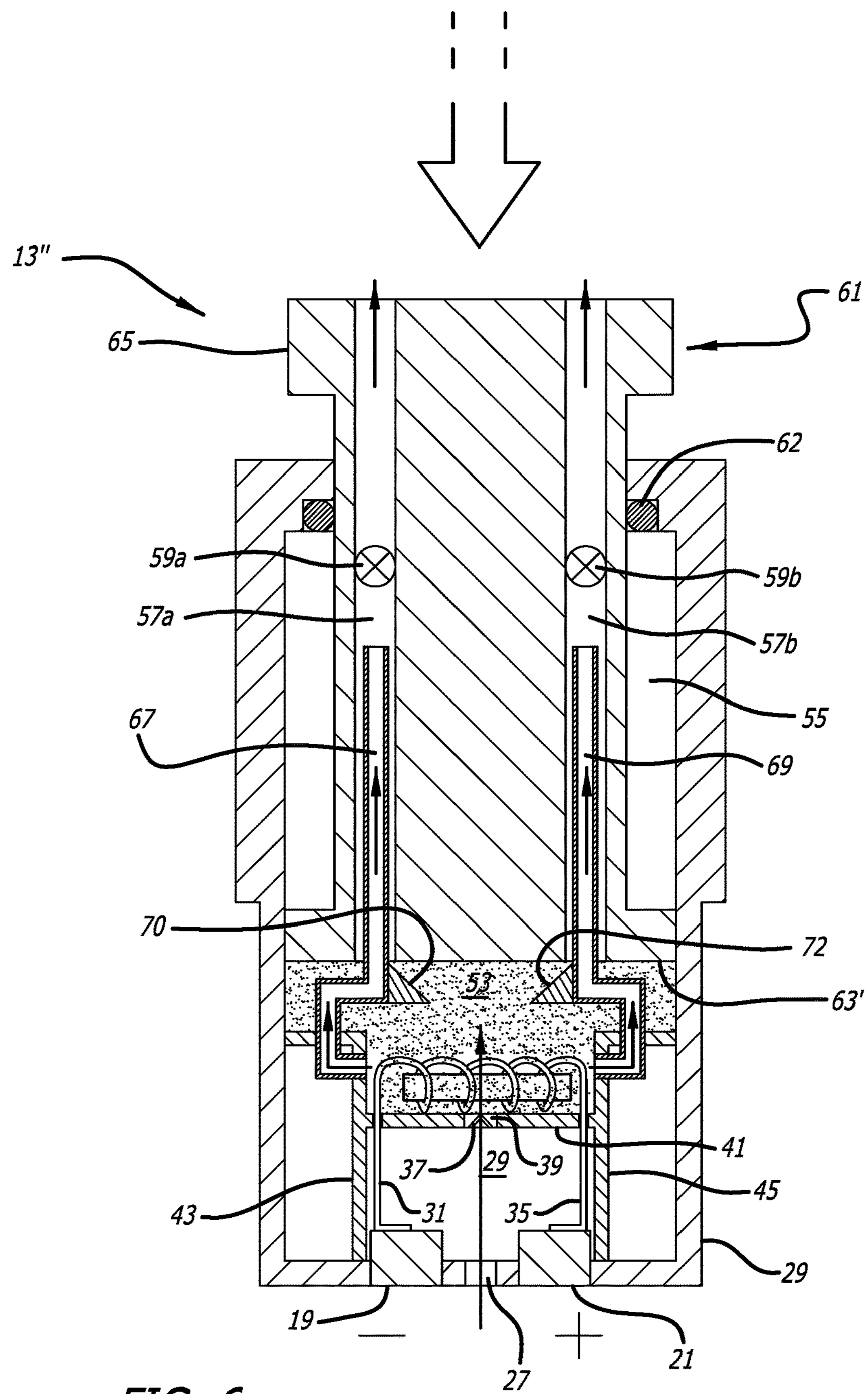
FIG. 6 is a sectional side view of the second alternative embodiment of the vape cartridge of the compact modular multifunctional inhalation device depicted in FIG. 5 with dual inhalation channels through a plunger in a second position in accordance with the present teachings.

FIG. 6 is a sectional side view of the second alternative embodiment of the vape cartridge of the compact modular multifunctional inhalation device depicted in FIG. 5 with dual inhalation channels through a plunger in a second down position in accordance with the present teachings. A bevel 70, 72 is provided within the chamber 55 and may be implemented with ceramic, nickel, quartz, stainless steel, silver or other suitable materials. The bevel 70 and 72 serves to funnel the tobacco, wax, shatter, butter, crumble, sauce, rosin, crystals or dab toward the coil 33 and rod 51.

Figure 7:
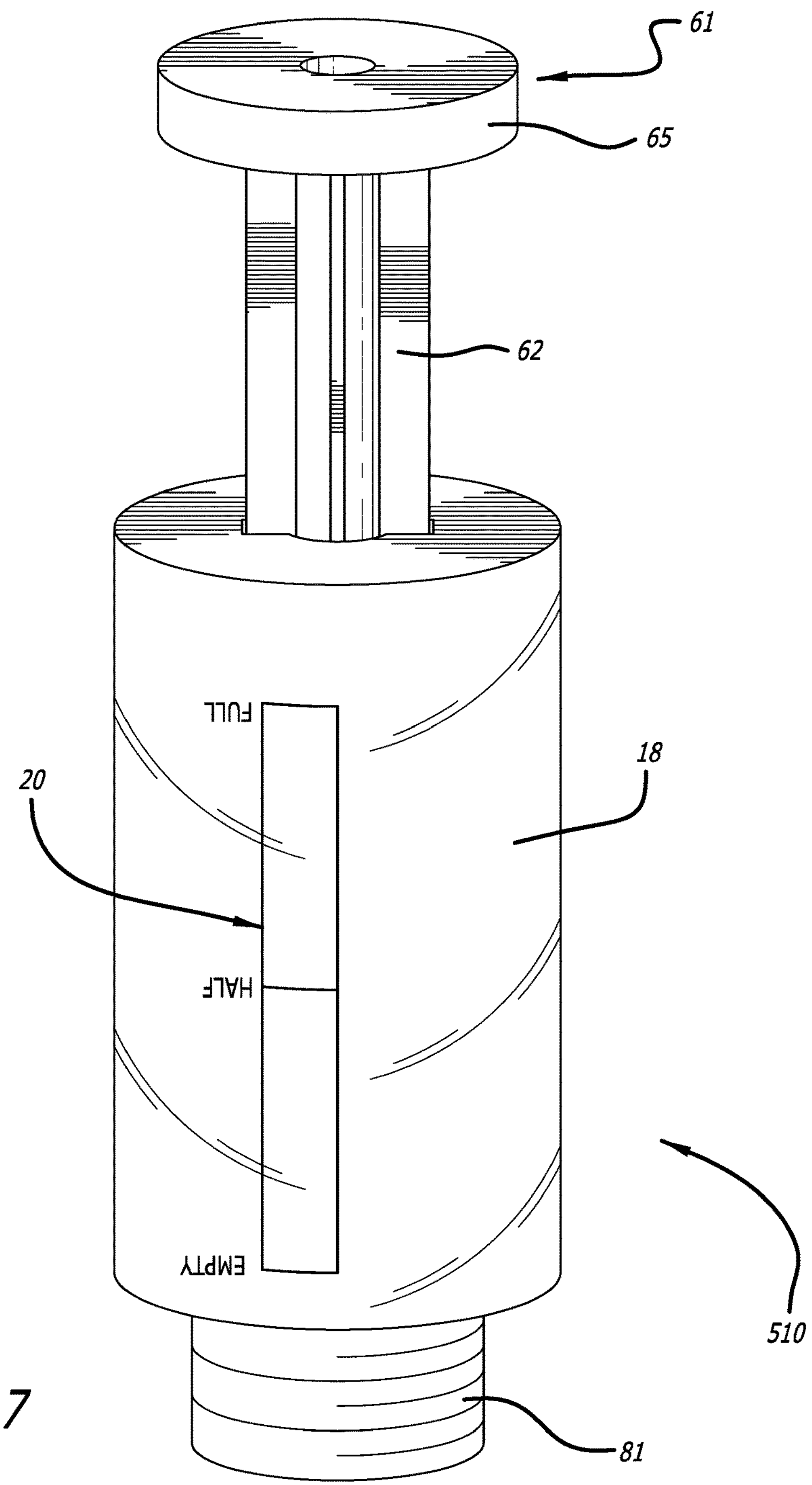
FIG. 7 is a side elevational perspective view of a '510' style cartridge in accordance with an alternative embodiment of the present teachings.

FIG. 7 is a side elevational perspective view of a cylindrical '510' style cartridge in accordance with an alternative embodiment of the present teachings. This embodiment features the plunger 61 and a gauge 20 implemented as transparent window of plastic or glass that shows the level of inhalant remaining in the chamber 55 (not shown) thereof.

Figure 8:
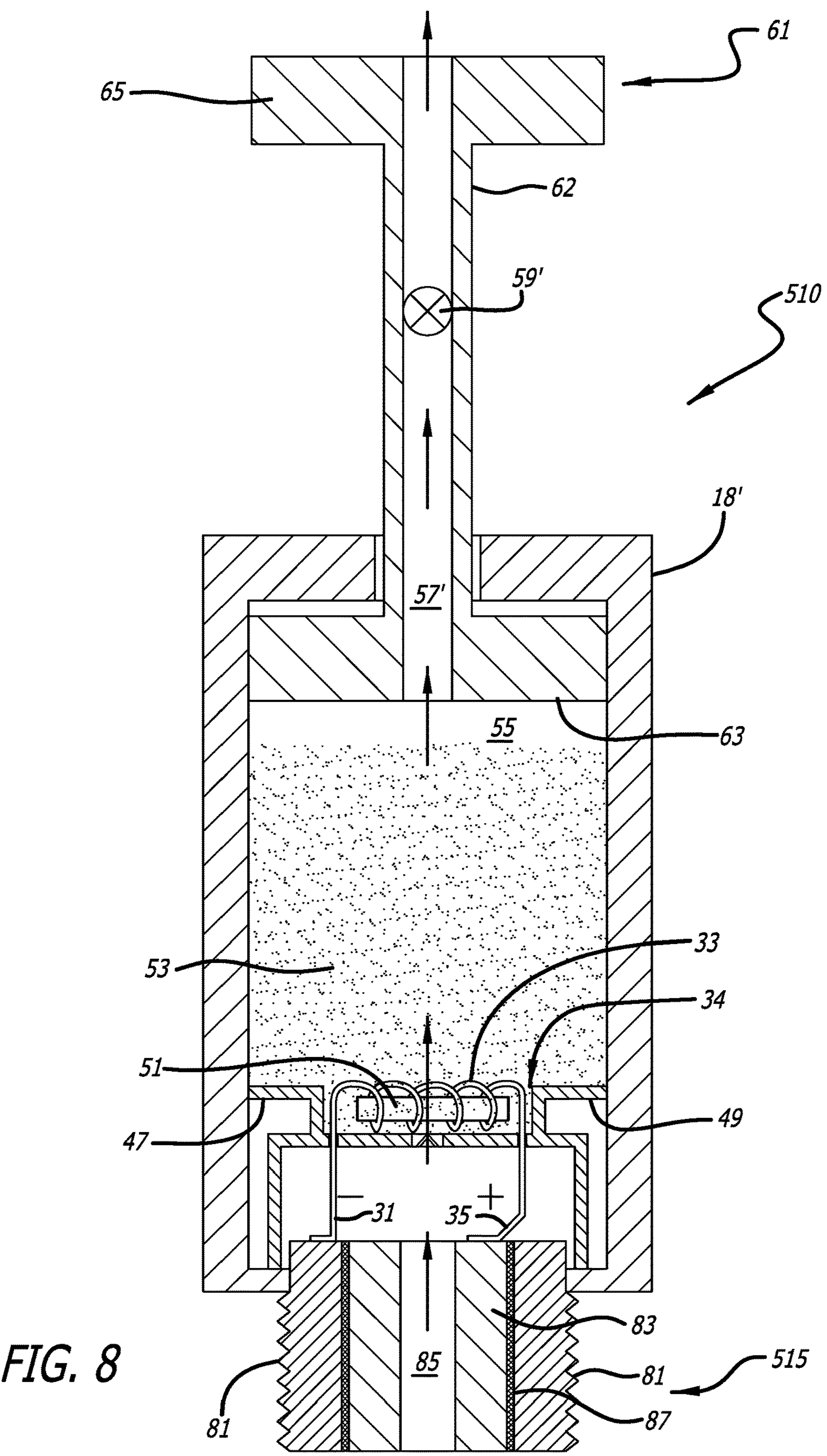
FIG. 8 is a sectional side view of the cartridge depicted in FIG. 7.

FIG. 8 is a sectional side view of the cartridge depicted in FIG. 7. As shown in this embodiment, the cartridge 510 includes a battery cartridge 515 that is threaded with an outer shell 81, an inner core 83 and an air inlet channel 85 therein.

Upon full threaded engagement with the upper section 18', the outer shell 81 of the battery cartridge 515 electrically couples to a first lead 31' of the coil 33' and the inner core 83 electrically couples to a second lead 35' of the coil 33'. A layer of insulation 87 is provided between the outer shell 81 and the inner core 83. The outer shell 81 may be fabricated of copper or aluminum, silver, brass, zinc, and gold The inner core 83 may be fabricated of copper or aluminum, silver, brass, zinc, and gold The layer of insulation 87 may be implemented with sand paper for grounding or other suitable insulator.

Figure 9:
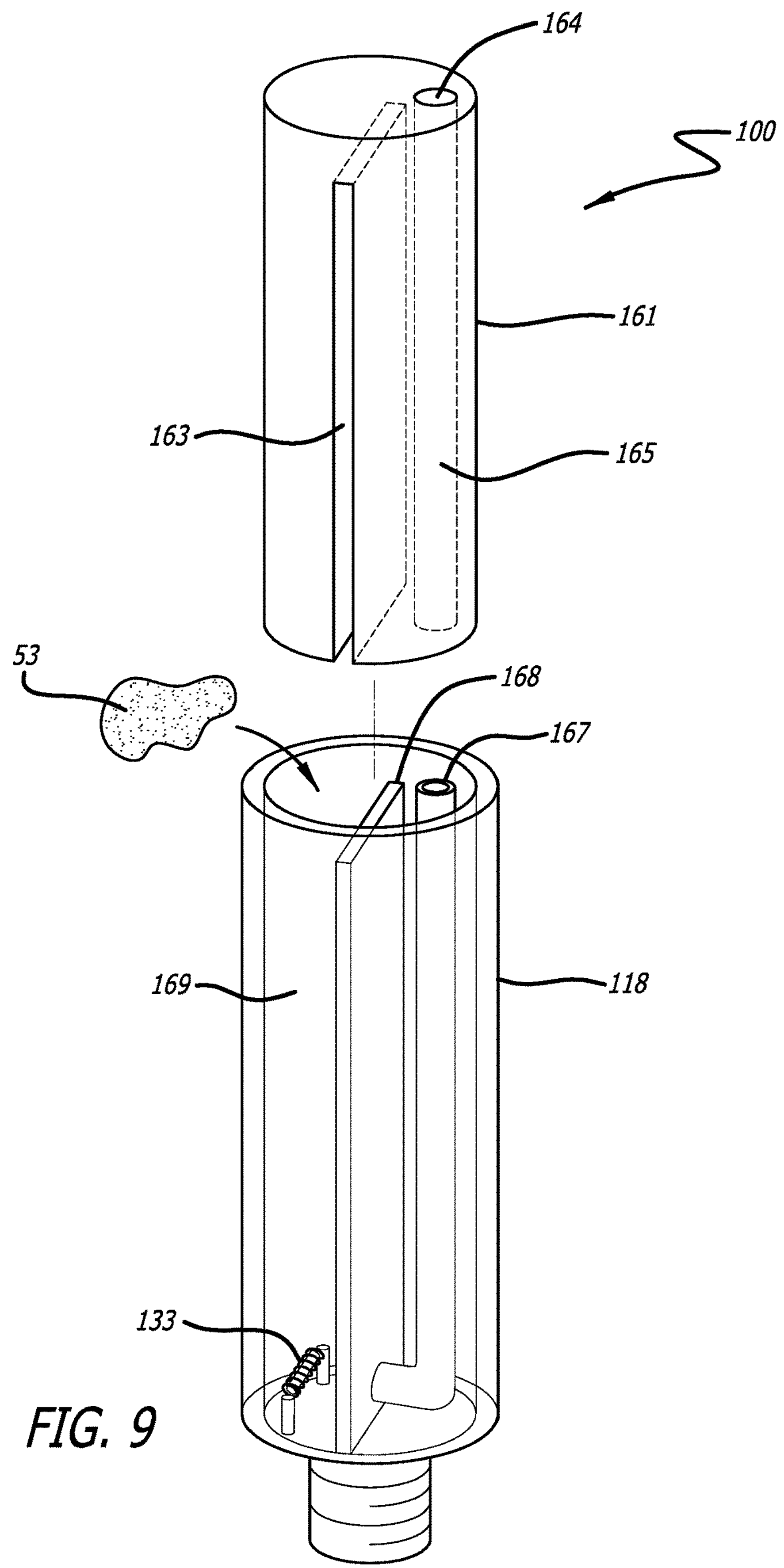
FIG. 9 is an alternative embodiment of the '510' style cartridge of FIG. 7.

FIG. 9 is an alternative embodiment of the cartridge of FIG. 7.

Figure 10A:
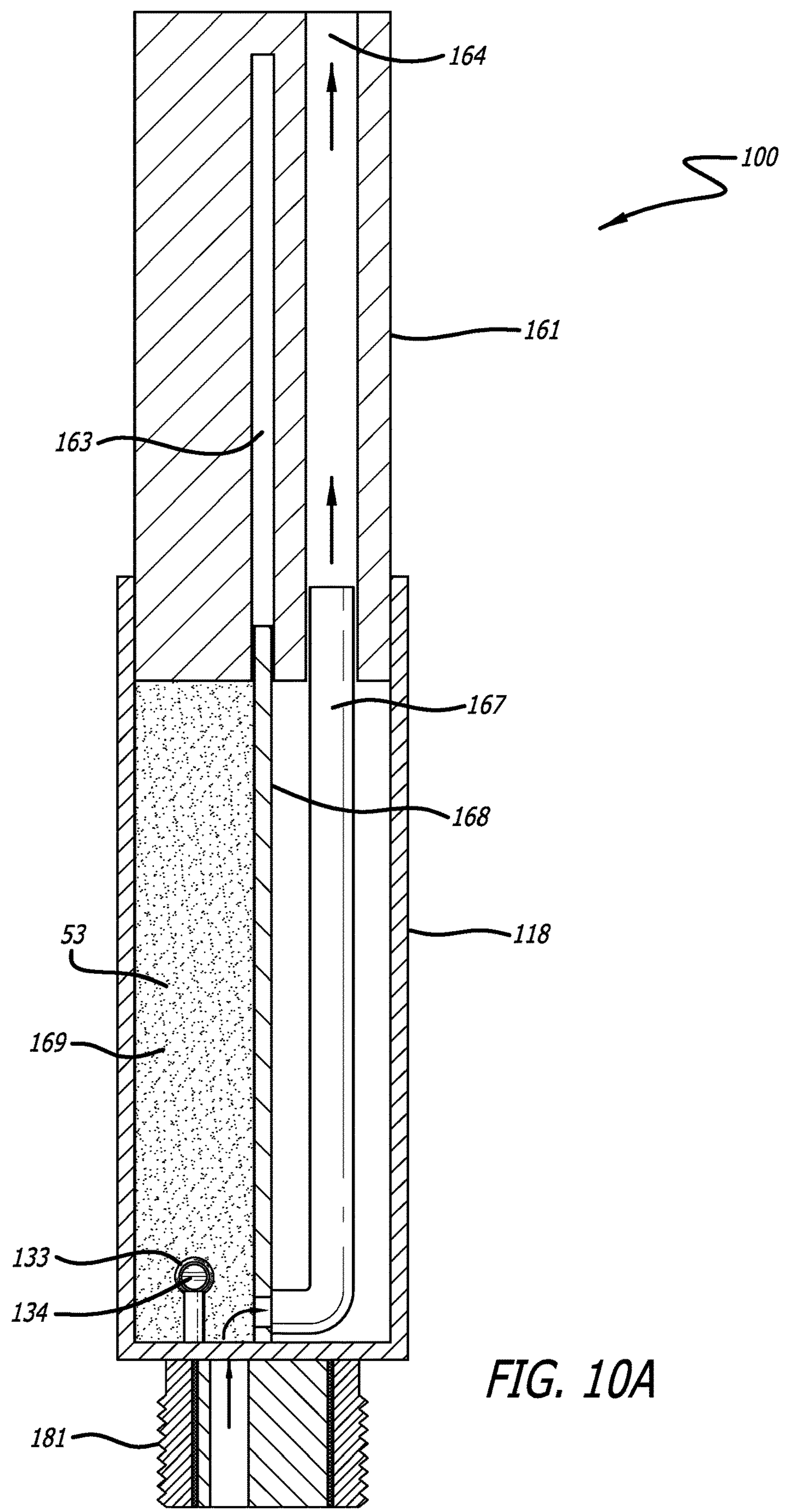
FIG. 10A is a sectional side view of the alternative embodiment of the cartridge depicted in FIG. 9 with the plunger thereof in a first position.

FIG. 10A is a sectional side view of the alternative embodiment of the cartridge depicted in FIG. 9 with the plunger thereof in a first position.

Figure 10B:
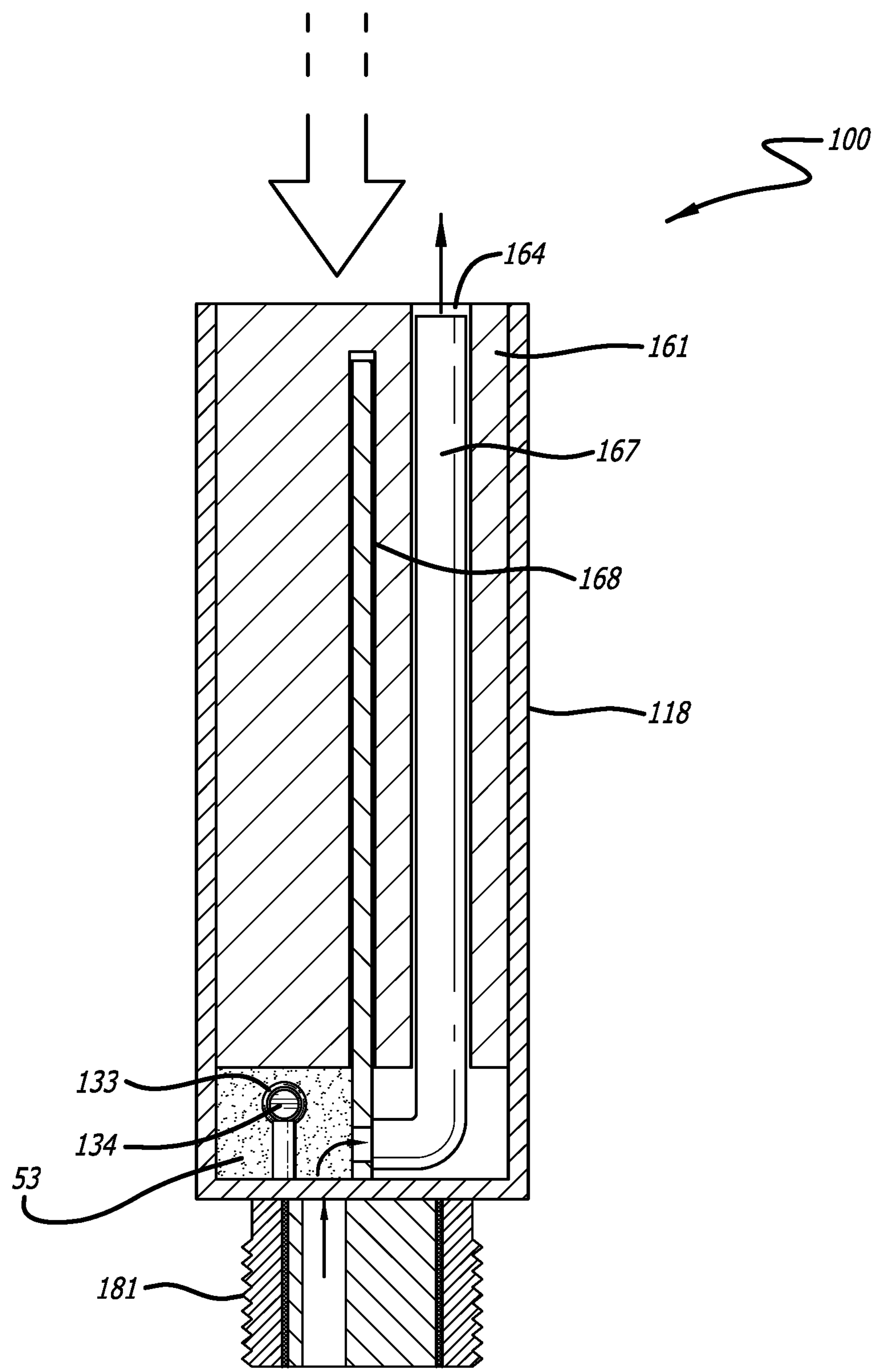
FIG. 10B is a sectional front view of the alternative embodiment of the cartridge depicted in FIG. 9 with the plunger thereof in a second position.

FIG. 10B is a sectional front view of the alternative embodiment of the cartridge depicted in FIG. 9 with the plunger thereof in a second position.

The cartridge 100 of FIGS. 9-10B includes vape cartridge 118 having a pipe 167 and a chamber divider 168. The chamber divider 168 provides a chamber 169 within which a coil 133 and rod quartz 134 are mounted. In practice, inhalant 53 is disposed within the chamber 169 for heating by the coil 133 and rod 134.

A plunger 161 is dimensioned for reciprocal motion within the cartridge 118 and has a mouthpiece 164 at the top of an outlet channel 165. The outlet channel 165 is adapted to receive the pipe 167. A recess 163 in the plunger 161 allows the plunger 161 to seat within the vape cartridge 118.

The alternative embodiments of FIGS. 9-10B allow for the same utility in a prismatic embodiment. In this context, a 'prismatic embodiment' refers a three-dimensional orthotope such as a right rectangular prism, rectangular cuboid, or rectangular parallelepiped. A special case of an n-orthotope, where all edges are equal length, is the n-cube to be used within a cylinder shaped cartridge.

In summary, some key features are the present invention are:

1. Orientation and number of metal straws within cartridge.
2. Adaptable Injection Plunger/mouthpiece inhaler hybrid lid.
3. Higher resistance coil and solid state wick exists internally.
4. The plunger and metal straws within the cartridge create a slide rail motion, when they are combined and a tray to keep the wax from escaping the coil.
5. Two air inhale pathways exist in this utility, as opposed to the one air passage typified by the prior art.
6. The Juul cartridge currently has no utility for waxy *cannabis* or nicotine concentrates, but rather low viscosity light & almost watery oils. *(All of the oils in the attached document below are not Juul cartridge compatible) air channels from within vape chamber are to the sides of the wick in mine. Juuls is orientated above the wick for the prismatic version.
7. 
8. Measurement glass cover gauge.
9. Allows for wax solids to be vaporized within cylindrical 5/10 threaded cartridge
10. Allows for long range use wax storage within vaporizing utensil instead of keeping wax in a regular container.
11. Fits to JUUL devices and any 5/10 threaded battery.
12. Smooth plunger within cartridge gliding action.

Those having ordinary skill in the art and access to the present teachings will recognize additional modifications, applications and embodiments within the scope thereof. For example, the invention is not limited to the size, shape, number or location of the input or output ports used in connection with the device or the material used in the construction of same.

The invention claimed is:

1. A compact modular multifunctional inhalation device comprising:

a housing having an inlet port and an outlet port;

a removable cartridge adapted to seat within the housing, the cartridge including:

a solid inhalant disposed within the cartridge and a heating element mounted within the cartridge for heating the inhalant;

a plunger adapted to translate within the cartridge, an air inlet port mounted on the cartridge, at least one vapor outlet port mounted within the plunger and at least one channel mounted within the plunger coupling the air inlet port and the at least one vapor outlet port, and dual channels mounted within the cartridge in communication with the inlet port.

2. The device of claim 1 wherein said heating element is a coil of metal or ceramic having 2-13 loops and a diameter of 1.3 mm-3.5 mm.

3. The device of claim 2 wherein said coil is mounted within a chamber in thermal proximity to said solid inhalant.

4. The device of claim 3 further including a quartz rod mounted within said coil.

5. The device of claim 1 further including a gauge mounted on said cartridge.

6. The device of claim 5 wherein said cartridge is at least partially transparent.

7. The device of claim 6 wherein said gauge is a measurement glass cover gauge.

8. A compact modular multifunctional inhalation device comprising:

a housing having an inlet port and an outlet port;

a removable cartridge module adapted to seat within the housing, the cartridge being a split chamber cartridge and including:

a heating element mounted within the cartridge for heating a solid inhalant and a split plunger adapted to translate the inhalant within the split chamber cartridge.

9. The device of claim 8 further including an air inlet port mounted on said cartridge, a vapor outlet port mounted within said plunger and a channel mounted within the plunger coupling the air inlet port and the vapor outlet port.

* * * * *